(12) United States Patent
Pan

(10) Patent No.: US 8,047,348 B2
(45) Date of Patent: Nov. 1, 2011

(54) CLUTCH STRUCTURE FOR MANUAL HOISTS

(76) Inventor: I-Te Pan, Taichung (TW)

( * ) Notice: Subject to any disclaimer, the term of this patent is extended or adjusted under 35 U.S.C. 154(b) by 403 days.

(21) Appl. No.: 12/381,002

(22) Filed: Mar. 9, 2009

(65) Prior Publication Data
US 2010/0213022 A1    Aug. 26, 2010

(30) Foreign Application Priority Data
Feb. 23, 2009 (TW) ................................ 98202606 U

(51) Int. Cl.
*F16D 7/06* (2006.01)
(52) U.S. Cl. ........................................ 192/56.62; 464/36
(58) Field of Classification Search ............... 192/54.52, 192/55.1, 56.6, 56.62, 93 A; 254/352–354, 254/365, 346, 347, 358, 372, 376; 464/35, 464/36
See application file for complete search history.

(56) References Cited

U.S. PATENT DOCUMENTS

| | | | |
|---|---|---|---|
| 2,587,712 A * | 3/1952 | Dodge | 464/36 |
| 2,948,173 A * | 8/1960 | Herrmann | 464/36 |
| 3,185,275 A * | 5/1965 | Orwin | 464/36 |
| 4,263,996 A * | 4/1981 | Putney | 464/36 |
| 4,348,011 A * | 9/1982 | Honda | 192/93 A |
| 4,372,433 A * | 2/1983 | Mitchell et al. | 192/93 A |
| 4,373,923 A * | 2/1983 | Kilwin | 464/36 |
| 4,768,754 A * | 9/1988 | Nishimura | 254/352 |
| 5,005,684 A * | 4/1991 | Fujii | 464/36 |
| 6,132,435 A * | 10/2000 | Young | 464/36 |
| 6,517,054 B2 * | 2/2003 | Samejima | 254/352 |
| 6,799,666 B2 * | 10/2004 | Kampf | |
| 2005/0167229 A1 * | 8/2005 | Tsukada et al. | 192/54.52 |

* cited by examiner

Primary Examiner — Gregory Binda
Assistant Examiner — Josh Skroupa

(57) ABSTRACT

A clutch structure for manual hoists includes a driven wheel for driving the wind device in the manual hoist. A ratchet and at least one resilient member are sequentially and co-axially mounted on the driven wheel. A nut is screwed onto the driven wheel to prevent the ratchet and the at least one resilient member from detaching from the driven wheel. The at least one resilient member axially pushes the ratchet to make the ratchet securely abut the driven wheel, and enhance the friction between the ratchet and the driven wheel, wherein the connecting intensity is the load limit of the manual hoist. The push force from the at least one resilient member to the ratchet is adjusted, and the friction between the ratchet and the driven wheel is adjusted when the position of the nut is adjusted.

6 Claims, 7 Drawing Sheets

US 8,047,348 B2

CLUTCH STRUCTURE FOR MANUAL HOISTS

BACKGROUND OF THE INVENTION

1. Field of the Invention

The present invention relates to a clutch structure, and more particularly to a clutch structure for manual hoists, which is automatically enforced upon an overload operation.

2. Description of Related Art

A manual hoist is a convenient mechanism for hoisting or unloading a heavy object. The manual hoist has a simple structure such that the manual hoist is widely used in many places.

The manual hoist usually includes a handle for sequentially driving a drive device and a wind device for to roll/release a chain or a cable to hoist/unload the heavy object. However, the conventional manual hoist has no clutch structure. Consequently, the operator frequently operates the manual hoist under an overload condition. As a result, the operator is located in a dangerous work place and the use life of the manual hoist is shortened due to an over abrasion.

Consequently, some manual hoist manufacturers provide a clutch structure between the drive device and the wind device for promoting the safety of the manual hoists. The conventional clutch structure of manual hoist includes two ratchets that are laterally abutted each other. A slip is formed between the two ratchets when the manual hoist is overload and the friction between the two ratchets is smaller than the load of the hoist such that the drive device can not drive the wind device to roll chain or cable.

However, a vibration may be occurred between the two ratchets and the two ratchets may be collided during clutching, especially when the hoist is in a heavy load. As a result, the use life of the ratchets is shortened even damaged during operating.

The present invention has arisen to mitigate and/or obviate the disadvantages of the conventional manual hoist and the clutch structure thereof.

SUMMARY OF THE INVENTION

The main objective of the present invention is to provide an improved clutch structure for manual hoists, which is easily manufactured and has a long use life.

To achieve the objective, the clutch structure in accordance with the present invention comprises a driven wheel adapted to drive a wind device in the manual hoist. The driven wheel includes a round body and a collar centrally and longitudinally extending from the body. A threaded portion is formed on a free end of the collar. One side of the body has multiple dimples equally defined in a circle that is a concentric circle relative to the body. A steel ball is partially received in each of the multiple dimples.

A ratchet is rotatably sleeved on the collar of the driven wheel for selectively driving the driven wheel when the load of the hoist is smaller than a connecting intensity between the ratchet and the driven wheel. The ratchet has a series of teeth formed on an outer periphery thereof. The series of teeth is adapted to be engaged to a handle such that the ratchet is driven and rotated when the handle is reciprocally operated. Multiple curved guide grooves are equally defined in one side of the ratchet and form a concentric circle relative to the ratchet. Each guide groove communicates with a corresponding one of the multiple dimples after assembling the ratchet such that the steel ball is received between the corresponding guide groove and dimple.

At least one resilient member is sleeved on the collar and abut against the ratchet for providing a lateral force to the ratchet and enhancing the connecting intensity between the ratchet and the driven wheel.

A nut is screwed onto the threaded portion of the collar to prevent the ratchet and the at least one resilient member from detaching from the driven wheel. The nut is provided to compress the at least one resilient member for promoting and adjusting the connecting intensity between the ratchet and the driven wheel.

Further benefits and advantages of the present invention will become apparent after a careful reading of the detailed description with appropriate reference to the accompanying drawings.

DETAILED DESCRIPTION OF THE INVENTION

Figure 1:
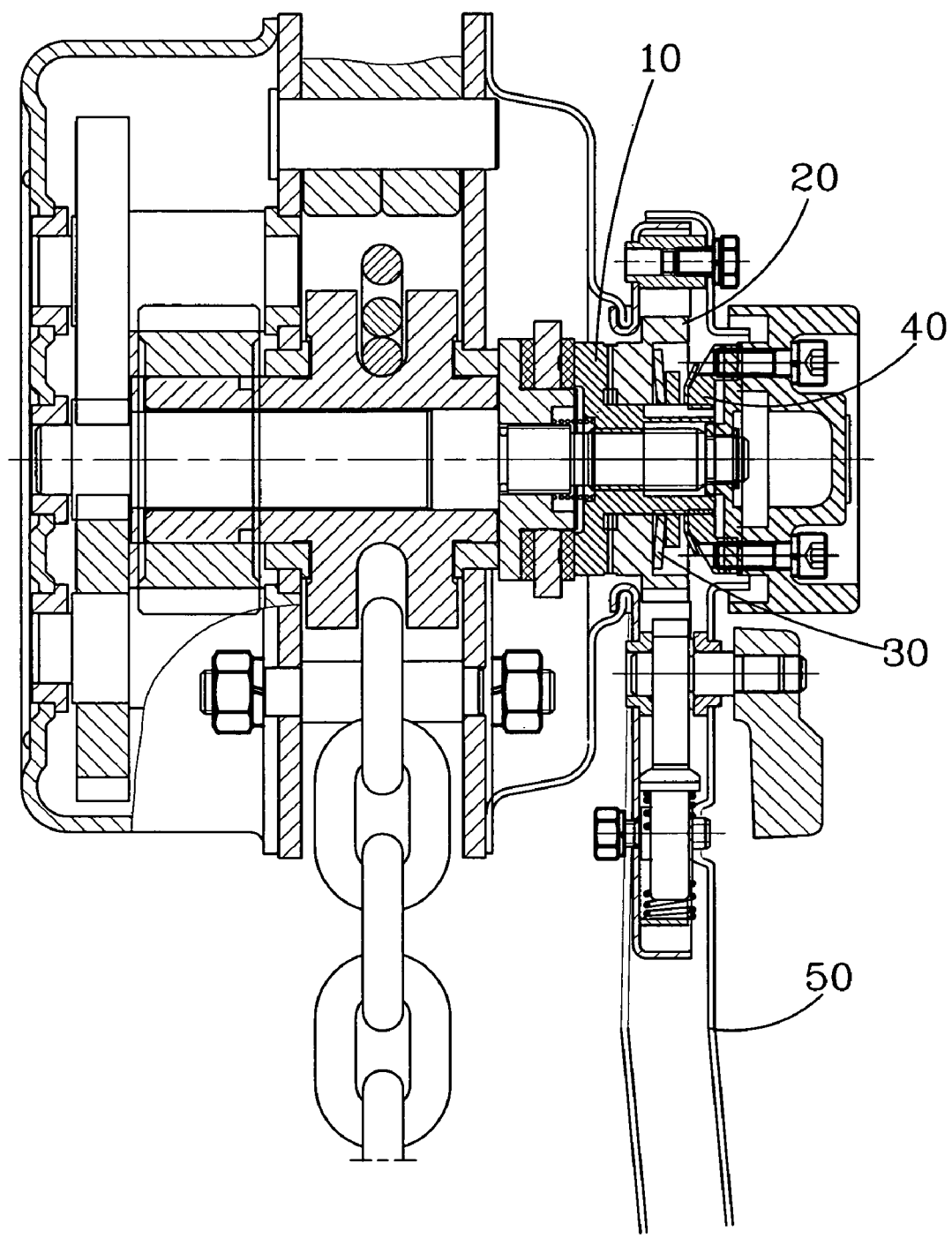
FIG. 1 is a schematic view of the clutch structure for manual hoist in accordance with the present invention.
Figure 2:
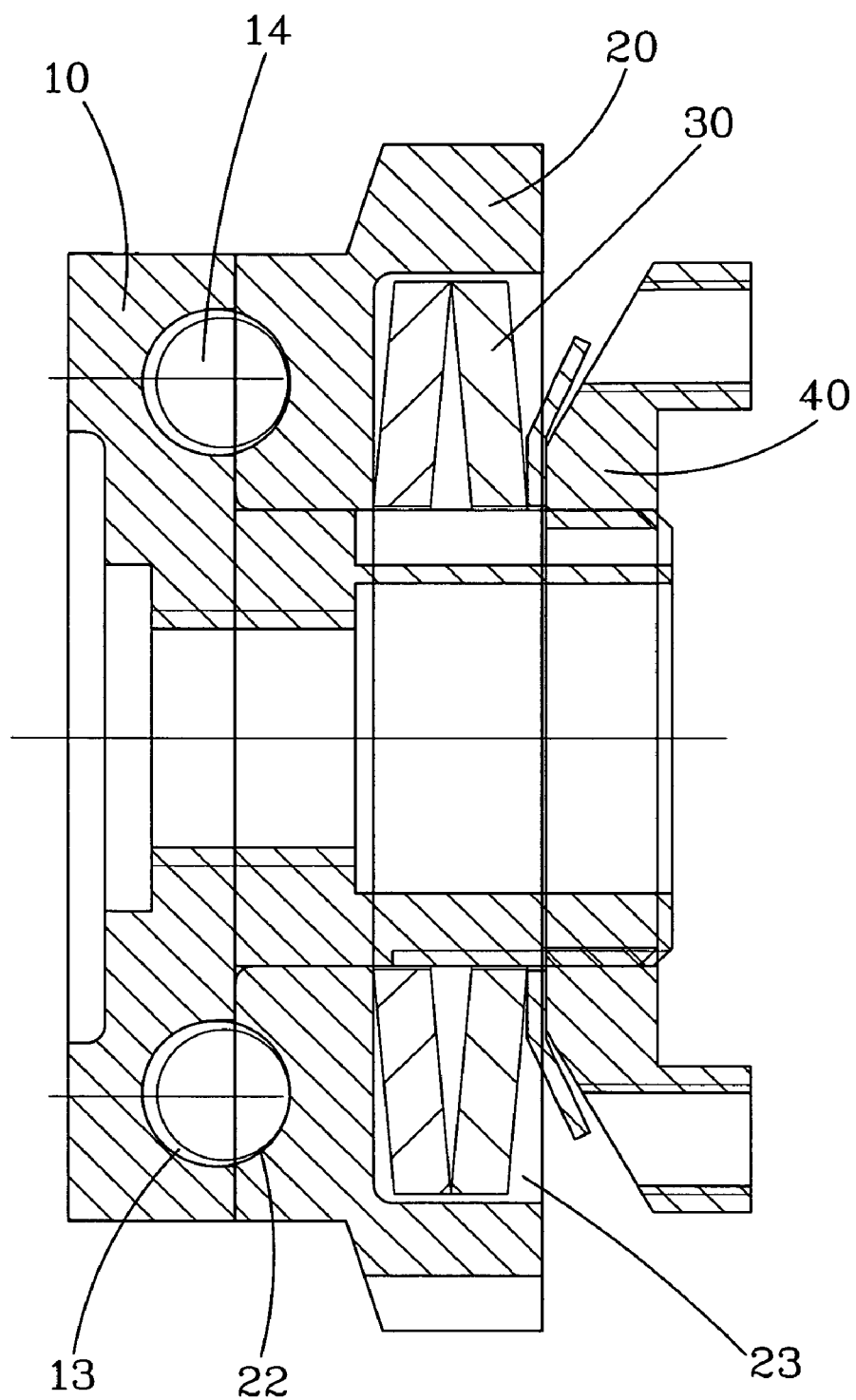
FIG. 2 is a cross-sectional view of the clutch structure in accordance with the present invention.

Referring to the drawings and initially to FIGS. 1 and 2, a clutch structure for manual hoists in accordance with the present invention comprises a driven wheel (10) adapted to drive the wind device (not numbered) in the manual hoist. A ratchet (20) and at least one resilient member (30) are sequentially and co-axially mounted on the driven wheel (10). Lastly, a nut (40) is screwed onto the driven wheel (10) to prevent the ratchet (20) and the at least one resilient member (30) from detaching from the driven wheel (10). The at least one resilient member (30) axially pushes the ratchet (20) to make the ratchet (20) securely abut the driven wheel (10), and enhance the friction between the ratchet (20) and the driven wheel (10), wherein the friction is the load limit of the manual hoist. Furthermore, the push force from the at least one resilient member (30) to the ratchet (20) is adjusted, and the friction between the ratchet (20) and the driven wheel (10) is adjusted when the position of the nut (40) is adjusted. Namely, the load limit of the clutch structure in accordance with the present invention is adjusted when the nut (40) is rotated.

Figure 3:
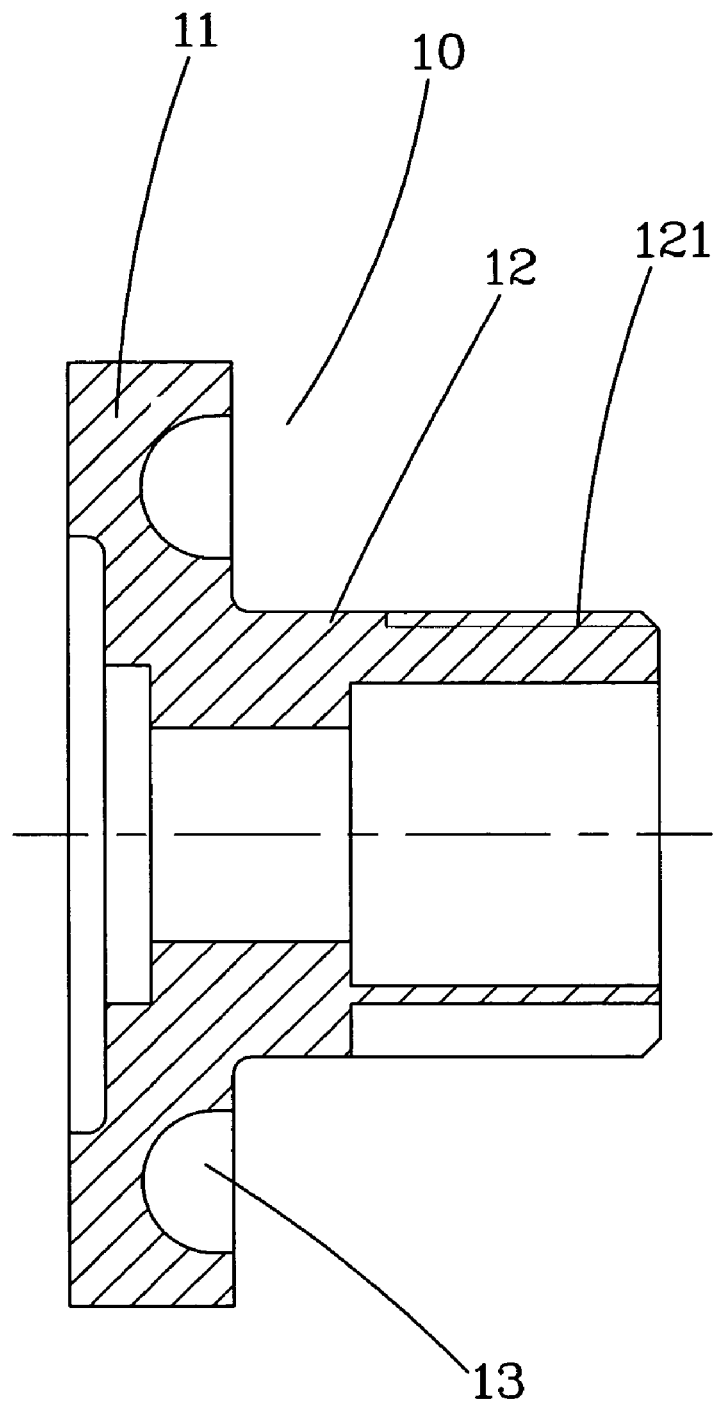
FIG. 3 is a cross-sectional view of a driven wheel of the clutch structure in accordance with the present invention.
Figure 4:
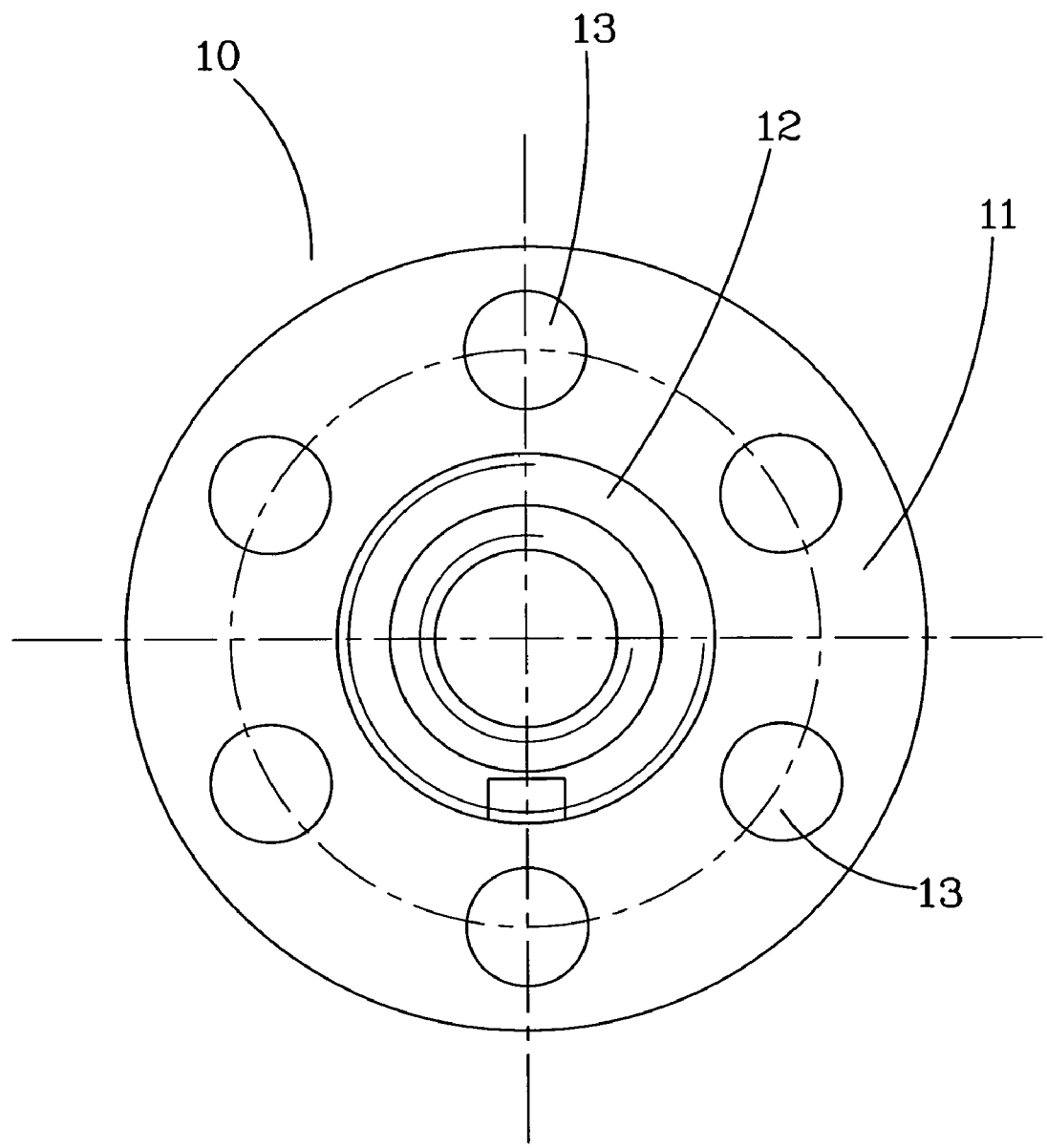
FIG. 4 is a front view of the driven wheel in FIG. 3.

With reference to FIGS. 2 to 4, the driven wheel (10) includes a round body (11), and a collar (12) centrally and longitudinally extending from the body (11). A threaded portion (121) is formed on a free end of the collar (12). One side of the body (11) has multiple dimples (13) equally defined in a circle that is a concentric circle relative to the body (10). A steel ball (14) is partially received in each of the multiple dimples (13).

Figure 5:
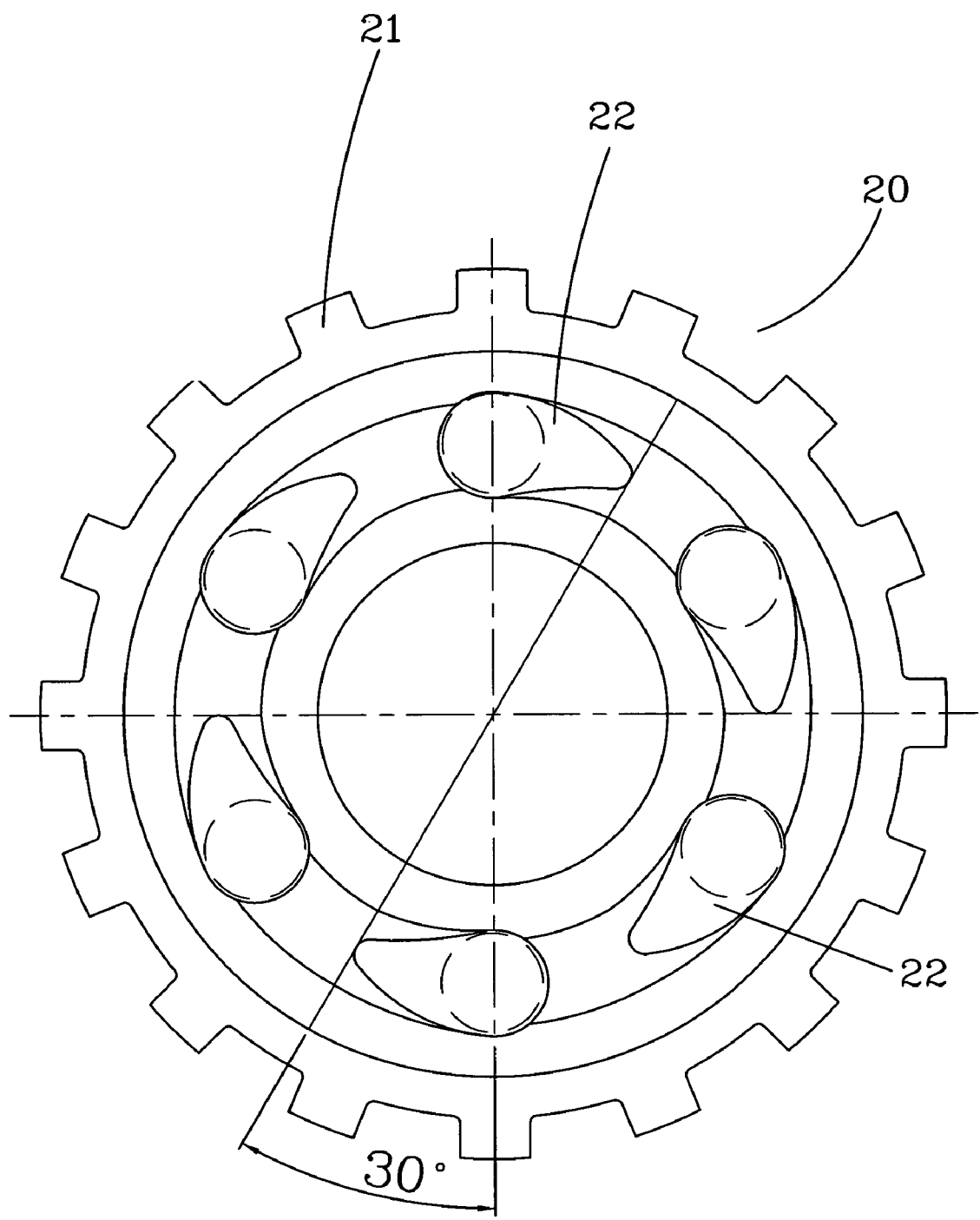
FIG. 5 is a rear view of a ratchet of the clutch structure in accordance with the present invention.
Figure 6:
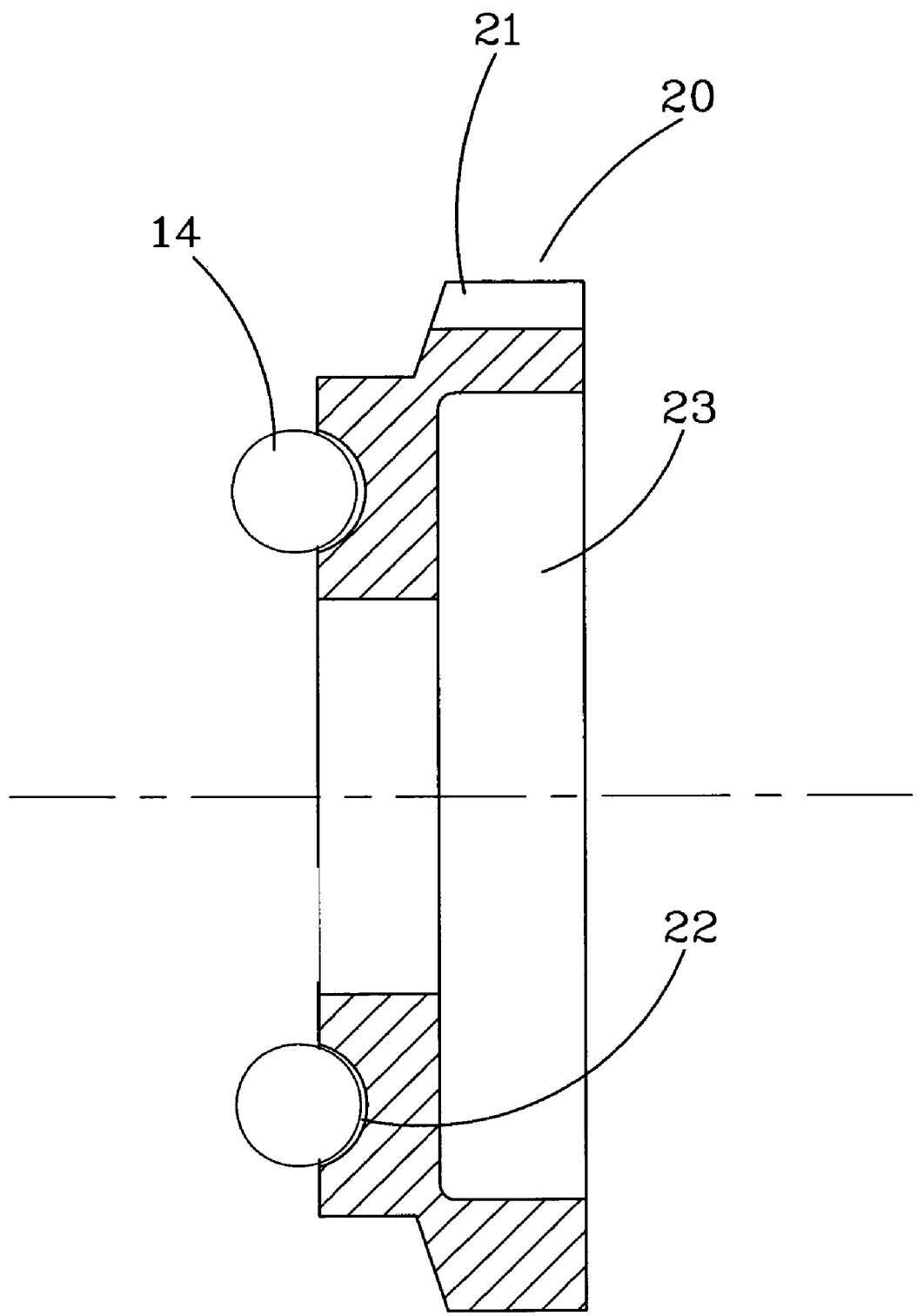
FIG. 6 is a cross-sectional view of the ratchet of the present invention.

With reference to FIGS. 2 and 5-6, the ratchet (20) is rotatably sleeved on the collar (12) of the driven wheel (10) and abuts against the body (11) of the driven wheel (10) for selectively driving the driven wheel (10). A slip condition is formed between the body (11) of the driven wheel (10) and the ratchet (20) when the load of the hoist is greater than the friction between the body (11) of the driven wheel (10) and the ratchet (20). As a result, the ratchet (20) can not drive the driven wheel (10) to make the hoist be operated.

Figure 7:
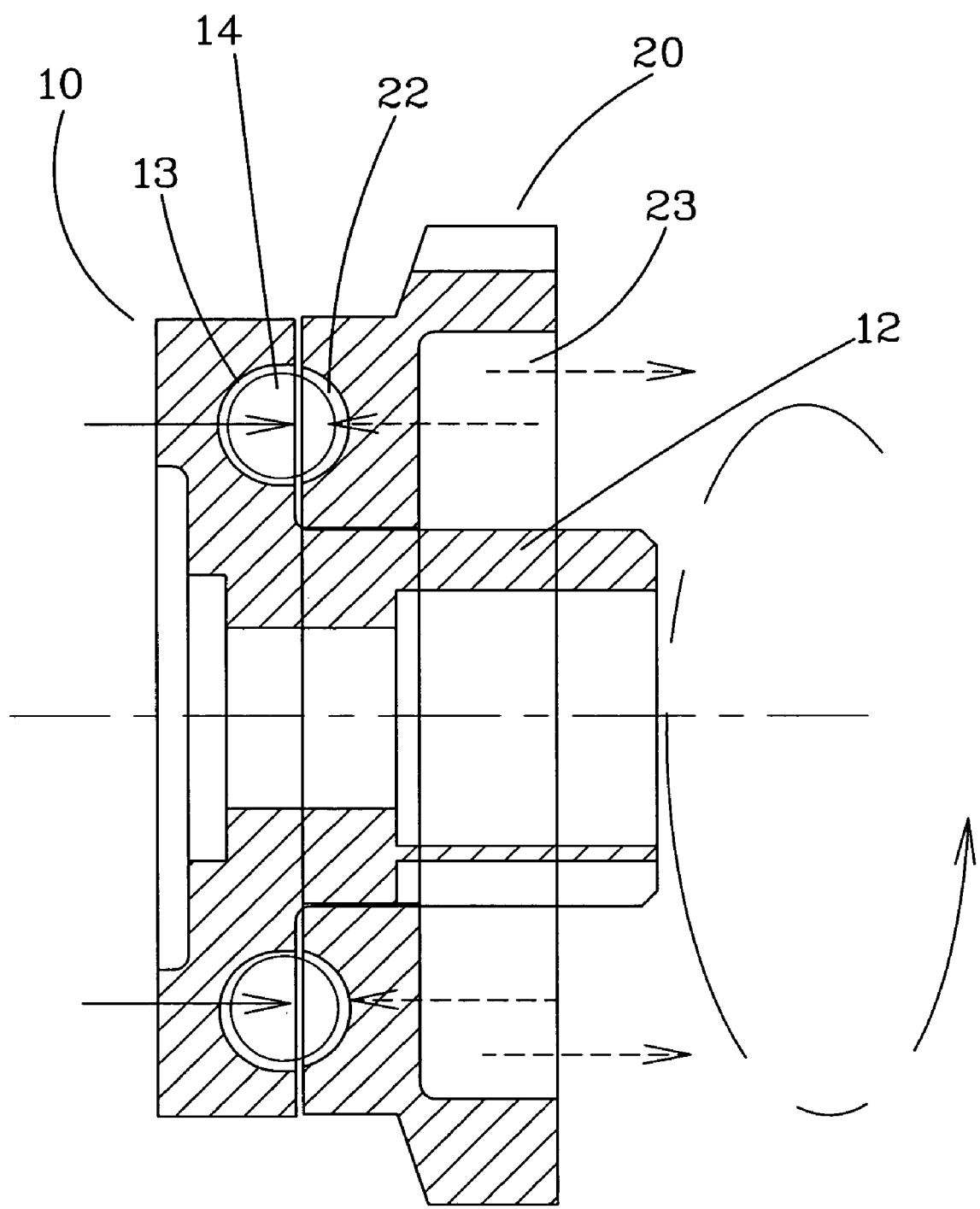
FIG. 7 is an operational view of the clutch structure in accordance with the present invention.

The ratchet (20) has a series of teeth (21) formed on an outer periphery thereof. The series of teeth (21) is adapted to be engaged to a handle (50), as shown in FIG. 1. The ratchet (20) is driven and rotated when the handle (50) is reciprocally operated. Multiple curved guide grooves (22) are equally defined in one side of the ratchet (20) and form a concentric circle relative to the ratchet (20). The radian of each of the multiple guide grooves (22) is 30 degrees. Each guide groove (22) communicates with a corresponding one of the multiple dimples (13) after assembling the ratchet (20) on the collar (12) of the driven wheel (10) such that the steel ball (14) is received between the corresponding guide groove (22) and the dimple (13). Each guide groove (22) is drop-shaped. The depth and the width of each of the multiple guide grooves (22) form a direct ratio. The maximum of the total depth of the dimple (13) and the guide groove (22) is slightly greater than the diameter of the steel ball (14), as shown in FIG. 7. A trough (23) is centrally defined in one side of the ratchet (20) opposite to the driven wheel (10).

With reference to FIG. 2, the at least one resilient member (30) is sleeved on the collar (12) of the driven wheel (10) and received in the trough (23) in the ratchet (20). The at least one resilient member (30) provides lateral force to the ratchet (20) to promote the connecting intensity between the ratchet (20) and the driven wheel (10). In the preferred embodiment of the present invention, there are two resilient members (30). The two resilient members (30) are disc springs and opposite to each other.

The nut (40) is screwed onto the threaded portion (121) of the collar (12) to prevent the ratchet (20) and the at least one resilient member (30) from detaching from the driven wheel (10). The nut (40) is provided to compress the at least one resilient member (30) for promoting the connecting intensity between the ratchet (20) and the driven wheel (10). Consequently, to adjust the position of the nut (40) can adjust the connecting intensity between the ratchet (20) and the driven wheel (10), and adjust the load limit of the manual hoist.

With reference to FIG. 7, the steel ball (14) is fully received between the guide groove (22) and the dimple (13) such that the ratchet (20) can successfully drive the driven wheel (10) via the steel balls (14) for hoisting the heavy object when the load of the hoist is smaller than the connecting intensity between the ratchet (20) and the driven wheel (10). When the load of the hoist is greater than the connecting intensity between the ratchet (20) and the driven wheel (10), the ratchet (20) can not drive the driven wheel (10) with the steel balls and is rotated relative to the driven wheel (10). At this time, the steel ball (14) is moved along the guide groove (22) and reversely pushes the ratchet (20) until received in a neighbor guide groove (22) for providing an overload alarm to the operator.

As described above, the clutch structure in accordance with the present invention includes the following advantages.

1. Easily to be manufactured: the main structures of the present invention are dimples (13), guide grooves (22) and steel balls (14). The dimples (13) and the guides (22) are respectively defined in the driven wheel (10) and the ratchet (20) such that they are easily processed. In addition, the steel ball (14) is widely marketed. Consequently, the manufacture cost can be greatly lowered.

2. The clutch structure in accordance with the present invention can solve the conventional problem of vibration during clutching. The depth of the guide groove (22) is gradually reduced and couple with the steel ball (14) that can effectively reduce the vibration between the ratchet (20) and the driven wheel (10) during clutching. As a result, the use life of the clutch structure in accordance with the present invention is lengthened.

Although the invention has been explained in relation to its preferred embodiment, it is to be understood that many other possible modifications and variations can be made without departing from the spirit and scope of the invention as hereinafter claimed.

What is claimed is:

1. A clutch structure for manual hoists, comprising:
    a driven wheel adapted to drive a wind device in the manual hoist, the driven wheel including a round body and a collar centrally and longitudinally extending from the body, a threaded portion formed on a free end of the collar, one side of the body having multiple dimples equally defined in a circle that is a concentric circle relative to the body, a steel ball partially received in each of the multiple dimples;
    a ratchet rotatably sleeved on the collar of the driven wheel for selectively driving the driven wheel when the load of the hoist is smaller than a connecting intensity between the ratchet and the driven wheel, the ratchet having a series of teeth formed on an outer periphery thereof, the series of teeth adapted to be engaged to a handle such that the ratchet is driven and rotated when the handle is reciprocally operated, multiple curved guide grooves equally defined in one side of the ratchet and form a concentric circle relative to the ratchet, each guide groove communicating with a corresponding one of the multiple dimples after assembling the ratchet such that the steel ball is received between the corresponding guide groove and dimple;
    at least one resilient member sleeved on the collar and abut against the ratchet for providing a lateral force to the ratchet and enhancing the connecting intensity between the ratchet and the driven wheel; and
    a nut screwed onto the threaded portion of the collar to prevent the ratchet and the at least one resilient member from detaching from the driven wheel, the nut provided to compress the at least one resilient member for promoting and adjusting the connecting intensity between the ratchet and the driven wheel;
    wherein each guide groove is drop-shaped, and the depth and the width of each of the multiple guide grooves form a direct ratio, the maximum of the total depth of the dimple and the guide groove slightly greater than the diameter of the steel ball, and the radian of each of the multiple guide grooves being 30 degrees.

2. The clutch structure as claimed in claim 1, wherein the ratchet has a trough centrally defined in one side thereof opposite to the driven wheel for receiving the at least one resilient member.

3. The clutch structure as claimed in claim 2, wherein there are two resilient members, the two resilient members being disc springs and opposite to each other.

4. The clutch structure as claimed in claim 1, wherein there are two resilient members, the two resilient members being disc springs and opposite to each other.

5. The clutch structure as claimed in claim 1, wherein the ratchet has a trough centrally defined in one side thereof opposite to the driven wheel for receiving the at least one resilient member.

6. The clutch structure as claimed in claim 5, wherein there are two resilient members, the two resilient members being disc springs and opposite to each other.

* * * * *